United States Patent [19]

Naruse et al.

[11] Patent Number: 5,594,149

[45] Date of Patent: Jan. 14, 1997

[54] PROCESS FOR PRODUCING 1,3-DIALKYL-2-IMIDAZOLIDINONE

[75] Inventors: Hiroshi Naruse; Hideki Mizuta; Shinichi Umeda; Teruyuki Nagata, all of Fukuoka-ken, Japan

[73] Assignee: Mitsui Toatsu Chemicals, Inc., Tokyo, Japan

[21] Appl. No.: 633,533

[22] Filed: Apr. 17, 1996

Related U.S. Application Data

[62] Division of Ser. No. 494,735, Jun. 26, 1995.

[30] Foreign Application Priority Data

Jul. 7, 1994 [JP] Japan .................................. 6-155763

[51] Int. Cl.$^6$ ...................... C07C 273/18; C07D 233/32; C07D 233/34

[52] U.S. Cl. .......................................... 548/316.4; 564/59

[58] Field of Search .............................. 548/316.4; 564/59

[56] References Cited

U.S. PATENT DOCUMENTS

| | | | |
|---|---|---|---|
| 2,340,045 | 1/1944 | D'Alelio et al. ........................... | 525/58 |
| 4,731,453 | 3/1988 | Nagata et al. ........................ | 548/316.4 |

FOREIGN PATENT DOCUMENTS 0198345  10/1986  European Pat. Off. .

*Primary Examiner*—Richard L. Raymond
*Attorney, Agent, or Firm*—Burns, Doane, Swecker & Mathis

[57] ABSTRACT

A novel bis-urea compound, preparation process of the compound, and preparation process of 1,3-dialkyl-2-imidazolidinone are disclosed and the disclosure provides a novel preparation process of 1,3-dialkyl-2-imidazolidinone and simultaneously enables effective utilization of N,N',N"-trialkyldiethylentriamine which lacks a large amount use and is desired to develop new application.

15 Claims, No Drawings

PROCESS FOR PRODUCING 1,3-DIALKYL-2-IMIDAZOLIDINONE

This application is a divisional of application Ser. No. 08/494,735, filed Jun. 26, 1995.

BACKGROUND OF THE INVENTION (1) Field of the Invention

The present invention relates to a novel bis-urea compound, a process for producing the compounds and a novel process for producing an aprotic polar compound 1,3-dialkyl-2-imidazolidinone represented by the formula (2):

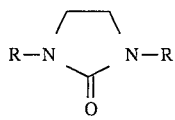
(2)

wherein R is an alkyl group, by using the bis-urea compounds.

The compounds represented by the formula (2) are a useful substance as an aprotic polar solvent and an intermediate for medicines and agricultural chemicals. The compounds are particularly excellent solvent for high polymers such as polyamides, polyvinyl chloride, polyvinyl alcohol, polystyrene, polyurethane and phenolic resins. Further, the compounds dissolve many inorganic compounds with ease and can be used as a solvent for various characteristic organic reactions.

(2) Prior Art of the Invention

Various processes have been proposed on the preparation of 1,3-dialkyl-2-imidazolidinones represented by the formula (2):

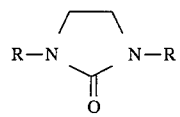
(2)

wherein R is an alkyl group. For example, on 1,3-dimethyl-2-imidazolidinone, a process wherein ethylenediamine is reacted with urea to obtain 2-imidazolidinone which is subjected to addition reaction to formaldehyde, followed by reducing the resulting reaction product with trichloroacetic acid, formic acid or the like, into the corresponding N,N'-dimethylated compound; a process having improved the above reducing process wherein hydrogenation decomposition is carried out using a noble metal catalyst in an acidic state; a process wherein N,N'-dialkylethylenediamine is reacted with phosgene or trichloroformate while it is decomposed into phosgene, etc. have been known.

The present inventors previously proposed a commercial process for producing 1,3-dialkyl-2-imidazolidinones in good yield by reaction of N,N'-dialkylethylenediamines with urea (U.S. Pat. No. 4,731,453). However, preparation of the raw material N,N'-dialkylethylenediamines from dichloroethane and alkylamines leads to formation of a by-product N,N',N''-trialkyldiethylenetriamines. Consequently, the yield of 1,3-dialkyl-2-imidazolidinones on the basis of dichloroethane is unsatisfactory in industry. For example, the yield is 68% in 1,3-dimethyl-2-imidazolidinone, 70% in 1,3-diethyl-2-imidazolidinone, 82% in 1,3-dipropyl-2-imidazolidinone and 85% in 1,3-dibutyl-2-imidazolidinone. Further, application of the by-product N,N',N''-trialkyldiethylenetriamines in a large amount has not yet been found and development of uses has been strongly desired.

SUMMARY OF THE INVENTION

A first object of the present invention is to provide a novel process for producing 1,3-dialkyl-2-imidazolidinones.

A second object of the present invention is to provide a preparation process which can be effectively utilized a by-product N,N',N''-trialkyldiethylenetriamines formed in preparing 1,3-dialkyl-2-imidazolidinones.

A third object of the present invention is to provide an useful intermediate, i.e. bis-urea compound, for producing the 1,3-dialkyl-2-imidazolidinones and a process for producing the intermediate.

As result of an intensive investigation for preparing the 1,3-dialkyl-2-imidazolidinones in order to achieve the above objects, the present inventors have found a novel process for producing the compounds through a novel substance which is obtainable by using N,N',N''-trialkyldiethylenetriamines as raw materials.

That is, the aspect of the present invention is;

1. a bis-urea compound represented by the formula (3);

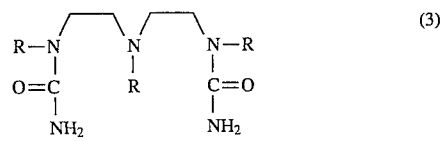
(3)

wherein R is an alkyl group, 2. a process for producing the bis-urea compound represented by the formula (3) comprising reacting N,N',N''-trialkyldiethylenetriamines represented by the formula (1):

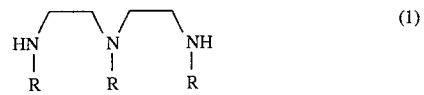
(1)

wherein R is an alkyl group, with urea.

3. a process for producing 1,3-dialkyl-2-imidazolidinones represented by the formula (2):

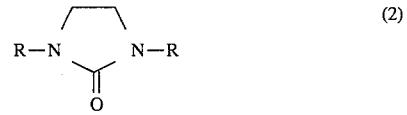
(2)

wherein R is an alkyl group, comprising heat-decomposing the bis-urea compounds represented by the formula (3).

4. a process for producing 1,3-dialkyl-2-imidazolidinones represented by the formula (2) comprising reacting N,N',N''-trialkyldiethylenetriamines represented by the formula (1) with urea, and successively heat-decomposing the resultant bis-urea compound without isolation.

The present invention enables to effectively utilize N,N',N''-trialkyldiethylenetriamine which lacks a large amount use and is desired to develop new application. Thus, the invention has great significance.

DETAILED DESCRIPTION OF THE INVENTION

N,N',N''-trialkyldiethylenetriamines used in the present invention represent by the above formula (1). Additionally, the bis-urea compounds represented by the formula (3) can be obtained by using the N,N',N''-trialkyldiethylenetriamines as raw materials. Further, the 1,3-dialkyl-2-imidazolidinones can be obtained by using the bis-urea compound as raw materials.

R in the formulas (1), (2) and (3) is alkyl groups, preferably an alkyl group having 1~8 carbon atoms, more preferably an alkyl group having 1–4 carbon atoms. Exemplary alkyl groups include a methyl group, ethyl group, n-propyl group, i-propyl group, n-butyl group, i-butyl group, s-butyl group, t-butyl group, n-pentyl group, i-pentyl group, t-pentyl group, n-hexyl group, i-hexyl group, n-octyl group and 2-ethylhexyl group.

N,N',N"-trialkyldiethylenetriamines used in the process of the invention can be preferably prepared by the reaction as shown in the reaction formula (A):

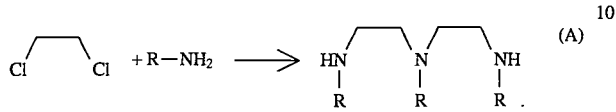

The compounds can also be prepared, when required, by reacting N,N'-dialkylethylenediamines with dichloroethane in the coexistence of an alkylamine.

In the preferred preparation of the raw material N N',N"-trialkyldiethylenetriamines, the molar ratio of alkylamine to 1,2-dichloroethane is preferably from 4 to 6. A high molar ratio of alkylamine is liable to increase the formation of N,N'-dialkylethylenediamines.

No particular limitation is imposed upon the temperature of the amination reaction as long as the temperature is in the range giving a suitable reaction velocity. The reaction temperature is preferably in the range of 80°–150° C.

The amination reaction is required to carry out under the application of pressure depending upon the reaction temperature.

The reaction mass of amination is neutralized with a suitable base such as sodium hydroxide and successively distilled to recover unreacted alkylamine. N,N',N"-Trialkyldiethylenetriamines formed is purified by distillation of the residual mass.

N,N',N"-Trialkyldiethylenetriamines thus obtained can be used in the preparation process of the present invention.

The bis-urea compounds represented by the formula (3) can be prepared by reacting the compound represented by the formula (1) with urea.

The reaction temperature is in the range of preferably 100°–155° C., more preferably 120°–145° C. The reaction temperature higher than 155° C. leads to decomposition of urea. On the other hand, when the reaction temperature is lower than 100° C., the reaction velocity becomes too slow.

Amounts of urea and N,N',N"-trialkyldiethylenetriamines used in the process of the present invention is urea of 1.0–3.0 moles, preferably 1.542.5 moles for a mole of N,N',N"-trialkyldiethylenetriamines. When urea is used in excess, solid impurities such as cyanuric acid which is a heat decomposition product of urea unfavorably remain in the reaction system. On the other hand, use of less than 1.0 mole ratio is unsuitable because an increased amount of by-product is formed.

The reaction progresses quantitatively and the end point of the reaction can be checked by determining ammonia gas which is liberated with the progress of the reaction.

The compounds of the formula (2) can be prepared by carrying out heat decomposition of the compounds of the formula (3).

The heat-decomposition is carried out at a temperature of preferably 180° C. or more, more preferably 200°–260° C., most preferably 210°–240° C. When the reaction temperature is lower than 180° C., the reaction velocity becomes slow. On the other hand, the reaction temperature around 300° C. unfavorably leads to problems on the heating means.

The compounds of the formula (2) also can be obtained by reacting the compounds of the formula (1) with urea, and successively by heat-decomposing the resultant compounds represented by the formula (3) without isolation.

A series of reaction for preparing the compounds of the formula (2) through the compounds of the formula (3) from the compounds of the formula (1) is illustrated in the reaction formula (B):

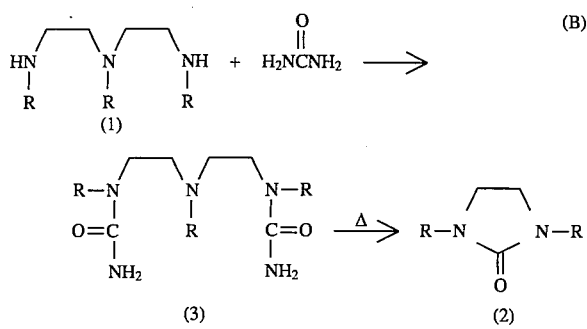

In this reaction, the reactions are carried out stepwise under the reaction conditions and the reaction temperature for preparing the compounds of the formula (3) and the compounds of the formula (2).

Reaction solvents can be used in all processes for preparing the compound of the formula (3) from the compounds of the formula (1), the compounds of the formula (2) from the compounds of the formula (3) and the compounds of the formula (2) from the compounds of the formula (1) without isolating the compounds of the formula (3), as exemplary solvent can be used in these processes include ethanol, methyl isobutyl ketone, N-methyl-2-pyrrolidone, 1,3-dimethyl-2-imidazolidinone, diethyleneglycol dimethyl ether, triethyleneglycol dimethyl ether and the like. However, it is desired for the process of the invention to carry out the reaction without solvent also in view of avoiding complex steps such as removal of the solvent by distillation.

1,3-Dialkyl-2-imidazolidinones formed are purified by distillation.

The present invention will hereinafter be illustrated further in detail by way of examples.

SYNTHESIS EXAMPLE 1

To a 5.0 liter pressure reactor equipped with a thermometer and stirrer, 1286.5 g (13 moles) of 1,2-dichloroethane and 2018.9 g (65 moles) of methylamine were charged and heated to 100° C. with stirring. Thereafter the amination reaction was carried out for 2 hours while maintaining the same temperature.

The reaction mixture was successively cooled to the room temperature and analyzed by gas chromatography. Conversion ratio of 1,2-dichloroethane was 100.0%.

Next, 1072.2 g of sodium hydroxide flake was charged to neutralize the reaction mixture and residual methylamine was recovered by distillation. The recovered methylamine was reused for the reaction. After distillation, sodium chloride which was separated in the reaction mass was filtered. The filtrate was distilled to obtain 229.4 g of N,N',N"-trimethyldiethylenetriamine.

EXAMPLE 1

(Synthesis of the Compound (3))

To a 0.5 liter flask equipped with a reflux condenser, thermometer and stirrer, 171.3 g (10 mole) of N,N',N"- trimethyldiethylenetriamine obtained in synthesis example 1 and 120.1 g (2.0 moles) of urea were charged and reacted for 3 hours with stirring while maintaining the temperature at 125°~140° C. After finishing the reaction, the reaction mass solidified at around 90° C. upon cooling. The solidified mass was ground and was dissolved in methanol at 60° C. Hexane was added to the solution and then the product crystallized out of the solution, the crystalline was filtered and dried. Thus 186.1 g of bis-urea compound was obtained in 80.2% yield. Melting point of the compound was 145°~147° C.

Chemical structure of the compound was identified with 1H NMR, 13C NMR, IR and FAB-MS(NH+/Z=232). Results of 1H NMR, 13C NMR and IR are as follows.

1H NMR; DMSO-d6 δ=2.2(s,3H), 2.4(t,4H), 2.8(s,6H), 3.2(t,4H). 5.8(s,br,4H)

13C NMR; DMSO-d6 δ=34(q), 42(q), 46(t), 55(t), 159(s).

IR; 1657 cm$^{-1}$(C=O)

EXAMPLE 2

(Synthesis of the Compound (2) From the Compound (3))

To 0.5 liter flask equipped with a reflux condenser, thermometer and stirrer, 115.7 g (0.5 mole) of the bis-urea compound obtained in Example 1 were charged and heated with stirring. The bis-urea compound began to melt at temperature of around 145° C. and leads to a complete fluid at temperature of 160° C. The temperature was raised up to 215°~225° C. and the reaction was carried out at the same temperature for 4 hours. After finishing the reaction the reaction fluid was cooled to obtain 1,3-dimethyl-2-imidazolidinone in 87.5% yield of formation according to gas chromatography.

EXAMPLE 3

To 0.5 liter flask equipped with a reflux condenser, thermometer and stirrer, 217.9 g (1.5 moles) of N,N',N"-trimethyldiethylenetriamine and 180.2 g (3.0 moles) of urea were charged and reacted for 4 hours with stirring while maintaining the temperature 125°~140° C. The temperature was raised up to 215°~225° C. and heat-decomposition was carried out at the same temperature for 4 hours. After finishing the decomposition, yield of formation of 1,3-dimethyl-2-imidazolidinone according to gas chromatography was 88.0% on the basis of N,N',N"-trimethyldiethylenetriamine.

The reaction mixture was successively distilled to obtain 137.0 g of 1,3-dimethyl-2-imidazolidinone. The product had purity of 99.3% and a boiling point of 105° C. under reduced pressure of 15 mmHg.

EXAMPLE 4

The reaction and analysis were carried out by the same procedures as described in Example 3 except that N,N',N"-trimethyldiethylenetriamine was replaced by N,N',N"-triethyldiethylenetriamine. As a result, 1,3-diethyl-2-imidazolidinone obtained had 85.4% yield of formation on the basis of N,N',N"-triethyldiethylenetriamine.

The reaction mixture was successively distilled to obtain 163.5 g of 1,3-diethyl-2-imidazolidinone. The product had purity of 99.4% and a boiling point of 109° C. under reduced pressure of 15 mmHg.

EXAMPLE 5

The reaction and analysis were carried out by the same procedures as described in Example 3 except that N,N',N"-trimethyldiethylenetriamine was replaced by N,N',N"-tripropyldiethylenetriamine. As a result, 1,3-dipropyl-2-imidazolidinone obtained had 81.2% yield of formation on the basis of N,N',N"-tripropyldiethylenetriamine.

The reaction mixture was successively distilled to obtain 184.6 g of 1,3-dipropyl-2-imidazolidinone. The product had purity of 99.6% and a boiling point of 110° C. under reduced pressure of 5 mmHg.

EXAMPLE 6

The reaction and analysis were carried out by the same procedures as described in Example 3 except that N,N',N"-trimethyldiethylenetriamine was replaced by N,N',N"-tributyldiethylenetriamine. As a result, 1,3-dibutyl-2-imidazolidinone obtained had 80.3% yield of formation on the basis of N,N',N"-tributyldiethylenetriamine.

The reaction mixture was successively distilled to obtain 210.1 g of 1,3-dibutyl-2-imidazolidinone. The product had purity of 99.6% and a boiling point of 127° C. under reduced pressure of 10 mmHg.

What is claimed is:

1. A process for producing a compound represented by the formula (3)

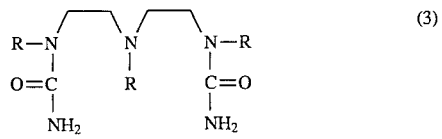

wherein is an alkyl group, comprising reacting N,N',N"-trialkyldiethylenetriamine represented by the formula (1);

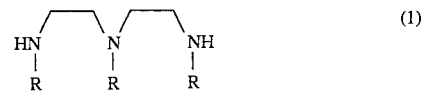

wherein R is an alkyl group, with urea.

2. A process according to claim 1 wherein the reaction temperature is 100°~155° C.

3. A process according to claim 1 wherein the reaction is carried out in the absence of a solvent.

4. A process according to claim 1 wherein R in the formulae (1) and (3) is an alkyl group having 1~8 carbon atoms.

5. A process according to claim 1 wherein R in the formulae (1)) and (3) is a methyl group.

6. A process for producing 1,3-dialkyl-2-imidazolidinone represented by the formula (2)

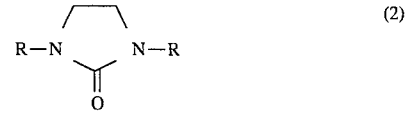

wherein R is an alkyl group, comprising heat-decomposing a bis-urea compound represented by the formula (3):

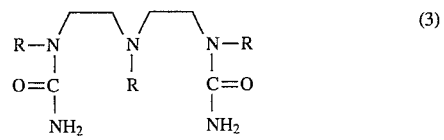

wherein R is an alkyl group.

7. A process according to claim 6 wherein the heat-decomposition temperature is 180° C. or more.

8. A process according to claim 6 wherein the heat-decomposition carried out in the absence of a solvent.

9. A process according to claim 6 wherein R in the formulae (2) and (3) is an alkyl group having 1~8 carbon atoms.

10. A process according to claim 6 wherein R in the formula (2) and (3) is an alkyl group having 1~4 carbon atoms.

11. A process for preparing 1,3-dialkyl-2-imidazolidinone represented by the formula (2)

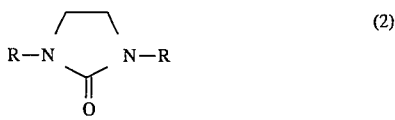

wherein R is an alkyl group, comprising reacting N,N',N''-trialkyldiethylenetriamine represented by the formula (1);

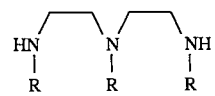

wherein R is an alkyl group, with urea and successively heat-decomposing the resultant bis-urea compound without isolation.

12. A process according to claim 11 wherein the bis-urea compound is formed at 100°~155° C. and heat-decomposed at 180° C. or more.

13. A process according to claim 11 wherein the reaction is carried out in the absence of a solvent.

14. A process according to claim 11 wherein R in the formulae (1) and (2) is an alkyl group having 1~8 carbon atoms.

15. A process according to claim 11 wherein R in the formulae (1) and (2) is methyl group.

* * * * *

UNITED STATES PATENT AND TRADEMARK OFFICE
CERTIFICATE OF CORRECTION

PATENT NO. : 5,594,149

DATED : January 14, 1997

INVENTOR(S) : Hiroshi NARUSE et al

It is certified that error appears in the above-identified patent and that said Letters Patent is hereby corrected shown below:

Column 6, line 35, in claim 1, after "wherein" insert --R--.

6, line 50, in claim 5, delete "(1))" and insert --(1)--.

Signed and Sealed this

Ninth Day of December, 1997

Attest:

BRUCE LEHMAN

Attesting Officer

Commissioner of Patents and Trademarks